(12) United States Patent
Kwak

(10) Patent No.: US 7,563,283 B2
(45) Date of Patent: Jul. 21, 2009

(54) NON-LINEAR ARTIFICIAL LIGAMENT SYSTEM

(75) Inventor: SeungKyu Daniel Kwak, Grafton, MA (US)

(73) Assignee: DePuy Spine, Inc., Raynham, MA (US)

( * ) Notice: Subject to any disclaimer, the term of this patent is extended or adjusted under 35 U.S.C. 154(b) by 736 days.

(21) Appl. No.: 11/171,022

(22) Filed: Jun. 30, 2005

(65) Prior Publication Data
US 2007/0005137 A1    Jan. 4, 2007

(51) Int. Cl.
*A61F 2/28*    (2006.01)
*A61F 2/30*    (2006.01)
*A61B 17/70*    (2006.01)

(52) U.S. Cl. .................. 623/17.11; 623/18.11; 606/257

(58) Field of Classification Search ............... 623/13.14, 623/13.11, 13.12, 13.13, 17.11, 20.24, 21.11, 623/21.12; 606/246–250, 252
See application file for complete search history.

(56) References Cited

U.S. PATENT DOCUMENTS

| | | | |
|---|---|---|---|
| 5,725,582 A * | 3/1998 | Bevan et al. ................ | 606/263 |
| 5,782,927 A | 7/1998 | Klawitter et al. | |
| 6,159,247 A | 12/2000 | Klawitter et al. | |
| 6,248,106 B1 * | 6/2001 | Ferree ........................ | 606/263 |
| 6,383,223 B1 * | 5/2002 | Baehler et al. ............ | 623/21.11 |
| 6,616,669 B2 * | 9/2003 | Ogilvie et al. .............. | 606/279 |
| 6,645,211 B2 * | 11/2003 | Magana ...................... | 606/247 |
| 6,652,585 B2 * | 11/2003 | Lange ..................... | 623/17.11 |
| 2004/0127989 A1 * | 7/2004 | Dooris et al. ............ | 623/13.17 |
| 2004/0236328 A1 * | 11/2004 | Paul et al. ...................... | 606/61 |
| 2005/0055096 A1 * | 3/2005 | Serhan et al. ............ | 623/17.11 |
| 2005/0101956 A1 * | 5/2005 | Simonson ..................... | 606/61 |
| 2005/0165486 A1 * | 7/2005 | Trieu ....................... | 623/17.13 |
| 2005/0216004 A1 * | 9/2005 | Schwab ........................ | 606/61 |
| 2005/0240266 A1 * | 10/2005 | Kuiper et al. ............ | 623/17.11 |

* cited by examiner

*Primary Examiner*—David Isabella
*Assistant Examiner*—Andrew Iwamaye
(74) *Attorney, Agent, or Firm*—Nutter McClennen & Fish LLP

(57) ABSTRACT

Various methods and devices for ligament replacement in the human body, and in particular, the spine are provided. In an exemplary embodiment, a ligament replacement system is provided that has an artificial ligament configured in the form of a closed loop. The artificial ligament is adapted to be coupled between the ligament seating regions of first and second connection members in a connection geometry that results in the artificial ligament having a large motion with a non-linear relationship between the force and displacement, similar to that of a natural ligament.

18 Claims, 15 Drawing Sheets

NON-LINEAR ARTIFICIAL LIGAMENT SYSTEM

BACKGROUND OF THE INVENTION

Ligaments are strong bands of fibrous tissue that can connect bones, such as the bones of the spinal column. There are two primary ligament systems in the spine, the intrasegmental system and the intersegmental system. The intrasegmental system holds the individual vertebrae together, and includes the ligamentum flavum, interspinous and intertransverse ligaments. The intersegmental system extends along the length of the vertebral column, and includes the anterior and posterior longitudinal ligaments, and the supraspinous ligaments.

Both of these ligament systems work in conjunction with the facet joints to provide structural stability and/or prevent excessive movement of the spinal column. Particularly, the ligamentous structures exhibit a non-linear relationship between motion and force, where initially little force is required for motion, and a greater additional force is required at larger motion. Further, these structures have properties that allow them to stretch a large amount before breaking.

Diseased, degenerated, impaired, or otherwise painful ligaments can require surgery to restore their function. While current artificial ligaments may relieve pain, they typically provide less motion than natural ligaments. Furthermore, many artificial joint replacements, such as spine, knee, hip, and shoulder, require extensive removal of the ligaments surrounding the joint. The functions of the ligaments removed should be restored to stability of the joint.

Accordingly, there remains a need for improved systems and methods to replace the ligaments of human body, and in particular, the spine.

SUMMARY OF THE INVENTION

The present invention provides an artificial ligament system that restores functions of a natural ligament. The artificial ligament system exhibits a non-linear force-displacement relationship in which the force required to move the joint increases non-linearly, similar to that of a natural ligament. Moreover, the artificial ligament system allows a large motion between bones while utilizing high strength low stretch fibers as an artificial ligament. One skilled in the art will appreciate that the artificial ligament system can work in conjunction with an artificial joint prosthesis, such as a facet joint prosthesis system, to restore the functions of natural ligaments. The artificial ligament system can be used in spinal applications as well as in other joints.

Disclosed herein are various methods and devices for ligament replacement in the human body, and in particular, the spine. In one aspect, a system for stabilizing adjacent bone segments is provided, and it can include an artificial ligament adapted to be contact at least two connection members in, for example, a closed loop. The artificial ligament can be coupled between first and second connection members and be in slidable contact with and to the ligament contact regions formed thereon.

The first and second connection members can have a variety of configurations that allow the artificial ligament to be in slidable contact therewith, however generally they can be substantially V-shaped or U-shaped connectors that are adapted to be positioned on a posterior surface of a first and second vertebrae. In one exemplary embodiment, the connection members are positioned such that they articulate with respect to one another.

The first and second connection members also have a ligament seating region and a ligament contact region. The ligament seating region can have any configuration that can hold the artificial ligament in place, such as a groove or a post. The post can have a groove or a stop formed therein to receive the artificial ligament, as well as to prevent it from sliding off the post. While the connection members can have any number of ligament contact regions, in an exemplary embodiment the first connection member can have at least one ligament contact region and the second connection member can have at least two ligament contact regions. The ligament contact region can have a configuration that allows the artificial ligament to slide thereover, and in an exemplary embodiment the ligament contact region is a smooth or curved surface. Alternatively, the ligament contact region can be a pulley or a pivot point. The ligament contact region generally has a surface area that is large enough to allow for contact with the artificial ligament, and, when the system includes two connection members, the surface area of the ligament contact region of the second connection member can be greater than that of the first connection member. This surface area differential results in the second connection member having at least two ligament contact regions, which are preferably located at opposed edges of the ligament seating region, and helps the artificial ligament exhibit a non-linear force displacement relationship.

One skilled in the art will appreciate that the closed loop configuration of the artificial ligament can be formed in a variety of ways. For example, the artificial ligament itself can be secured by suturing, stapling, knotting, etc. one end of the artificial ligament to the other end of the artificial ligament. Alternatively, the artificial ligament can be attached to one of the first or second connection members, and looped over the other connection member to effect a pulley type motion. While the artificial ligament does not have to be specifically adapted for attachment directly to the first or second connection member, in one embodiment, the artificial ligament has two eyelets formed on opposed ends thereof that can receive a fastener, which in turn can be secured to the first or second connection member.

In another aspect, a system for stabilizing adjacent bone segments can include an artificial ligament that is adapted to be configured in the form of a closed loop. The artificial ligament can be coupled between first, second, and third connection members and be slidably moveable within the ligament seating regions of each member. The first, second and third connection members can have any configuration that allows the artificial ligament to be slidably movable thereover, however in an exemplary embodiment the connection members are posts that are adapted to be coupled to adjacent bone segments.

The artificial ligament-connection member combination can have a variety of different arrangements to effect a non-linear force-displacement relationship. In one exemplary embodiment, the connection members are arranged in a triangular configuration where the first connection member is placed on a first bone segment and the second and third connection members are placed in a spaced relationship on a second bone segment. This configuration can also be reversed such that the second and third connection members are placed on the first bone segment, and the first connection member is placed on the second bone segment. Alternatively, the system can include a fourth connection member that is placed in a spaced relationship to the first connection member. This can result in the artificial ligament being coupled to the connection members in substantially an "x-shaped" configuration.

The posts can hold the artificial ligament by a variety of mechanisms. In one exemplary embodiment, the posts can have a groove or a stop formed therein. The posts can also have a variety of configurations that allow the artificial ligament to be slidably moveable therewith. For example, a portion of the post can be curved or smooth, or a pulley or a pivot point.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
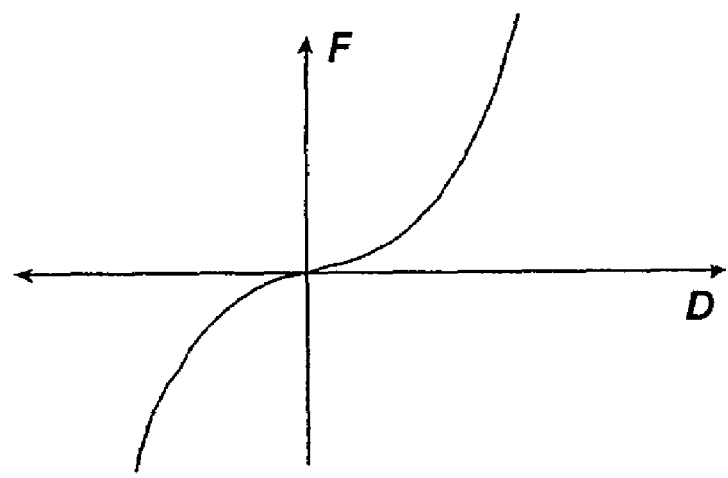
FIG. 1 is a graph showing the non-linear force-displacement of a natural ligament.

Disclosed herein are various methods and devices for ligament replacement in a body, and in particular, for replacement of ligaments in the spine. In one exemplary embodiment, a ligament replacement system is provided that has an artificial ligament configured in the form of a closed loop. The artificial ligament is adapted to be coupled between the ligament seating regions of at least first and second connection members in a connection geometry that results in the artificial ligament having a large motion with a non-linear relationship between the force F and displacement D. This non-linear force-displacement relationship approximates that of a natural ligament as shown in FIG. 1. A person skilled in the art will appreciate that, while the methods and devices are especially configured for restoring and/or replacing the ligaments of the spine, the methods and devices can be used to replace a variety of other ligaments in the human body, including, without limitation, those found in the hand, knee, foot and shoulder. Moreover the systems disclosed herein can be incorporated with artificial joint prosthesis systems.

While a variety of artificial ligaments can be used with the systems disclosed herein, in an exemplary embodiment, a conventional artificial ligament made from a low friction, high strength fiber can be used. Exemplary fibers include polyethylene, polyester, polypropylene, carbon fiber, glass, glass fiber, polyurethane, polyaramide, polymers, copolymers, polyactic acid (PLA), polyglycolic acid (PGA), silk, cellusoseic acid, and polycaprolactone fibers. One skilled in the art will appreciate that the artificial ligament can have any configuration that allows for the properties noted above, such as linear or braided.

While both the stretch and the tensile strength requirements of the fibers will vary depending upon the system configurations and the amount of ligament stretch and/or strength desired, in an exemplary embodiment the stretch of the fibers can be less than 5%, and more preferably in the range of about 1% to 2%, and the tensile strength of the fibers can be greater than 100N, and preferably in the range of about 100N to 10,000N.

One skilled in the art will further appreciate that high strain artificial ligaments, that is, ligaments having a strain in the range of about 5% to 25%, can also be used with the systems described herein. This is particularly advantageous in that previous uses of high strain artificial ligaments have resulted in a linear force-displacement relationship that does not mimic the natural ligament, and results in a greater likelihood of the artificial ligament breaking.

Any number of artificial ligaments can be used with the system disclosed herein depending upon the desired amount of lateral support and motion. Generally, the greater the number of artificial ligaments that are used, a greater the amount of support, and a lesser amount of motion, e.g., flexion, extension, rotation, and lateral bending, is afforded to a patient. Thus, an embodiment that includes two artificial ligaments 12a, 12b, such as that shown in FIGS. 2A-3B, provides more support to a patient and allows the patient a smaller range of motion when compared to an embodiment that includes one artificial ligament 112, e.g., the embodiment shown in FIG. 4. These embodiments will be discussed in more detail below.

Referring now to FIGS. 2A-3B, an exemplary system 10 for stabilizing adjacent bone segments is shown that includes an artificial ligament 12a, 12b that is adapted to be configured in the form of a closed loop, and a first connection member 14 that is adapted to couple to a first bone segment 30, such as a superior vertebra, and a second connection member 64 that is adapted to couple to a second bone segment 80, such as an inferior vertebra. The first and second connection members 14, 64 have a ligament seating region 16, 17, 66, 67 (shown in FIG. 3A) and each connection member 14, 64, can have at least one a ligament contact region (not shown). The artificial ligament 12a, 12b is adapted to couple between the first and second connection members 14, 64 in any connection geometry that allows it to have a non-linear force-displacement relationship, and such that it is held within the ligament seating region 16, 17, 66, 67 and is in slidable contact with the ligament contact regions. The various connection geometries will be discussed in more detail below.

Figure 2A:
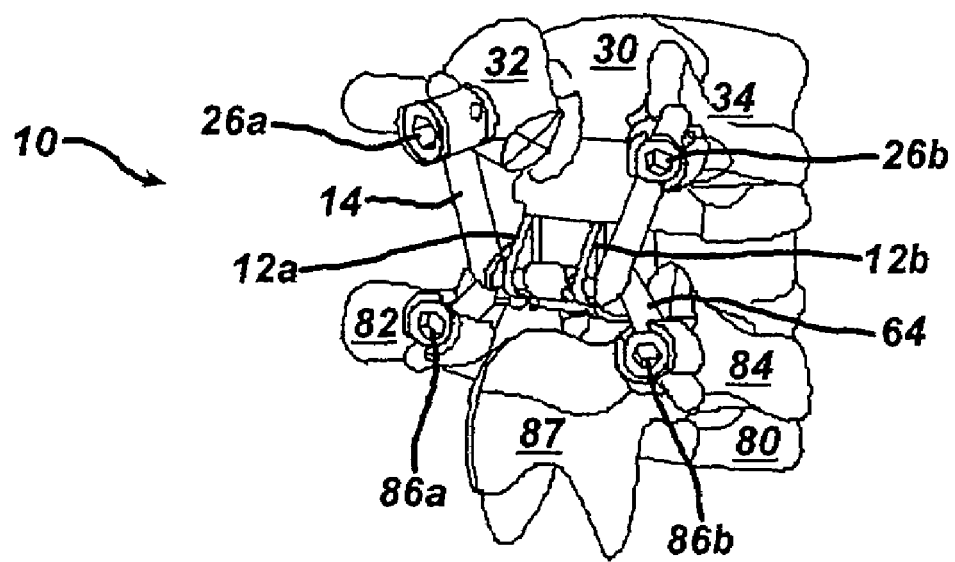
FIG. 2A is a side perspective view of one exemplary system for stabilizing bone segments as disclosed herein in the neutral position.
Figure 2B:
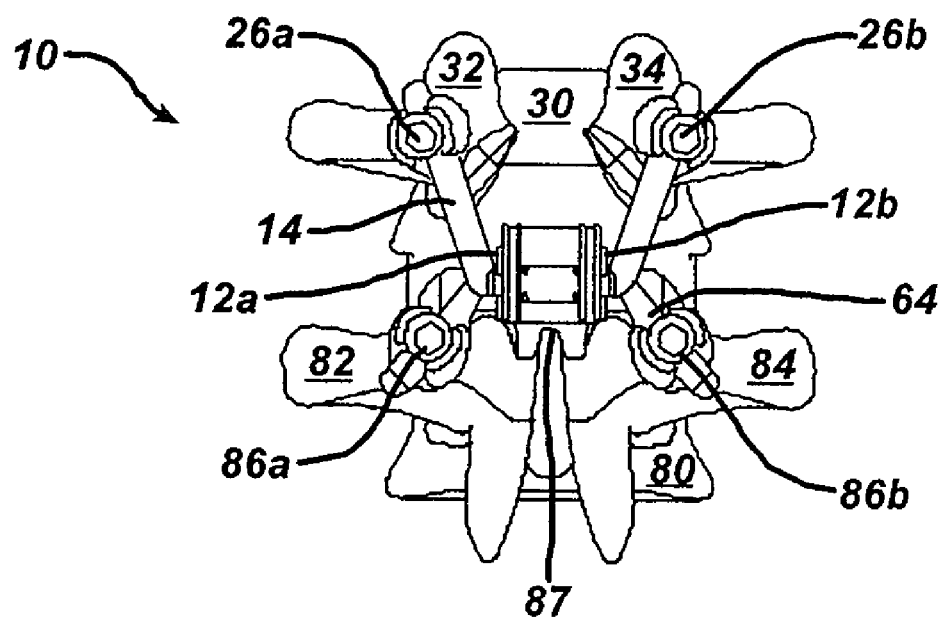
FIG. 2B is a posterior view of the system of FIG. 2A.
Figure 2C:
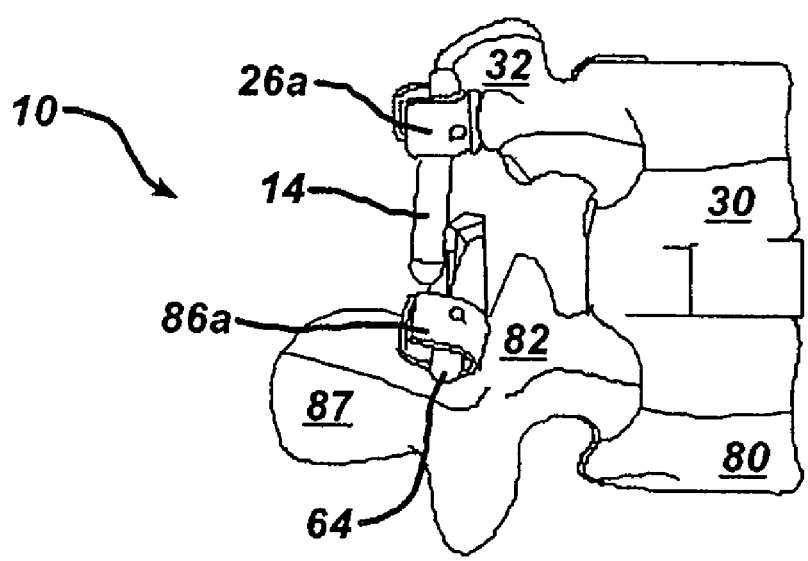
FIG. 2C is side view of the system of FIG. 2A.
Figure 3A:
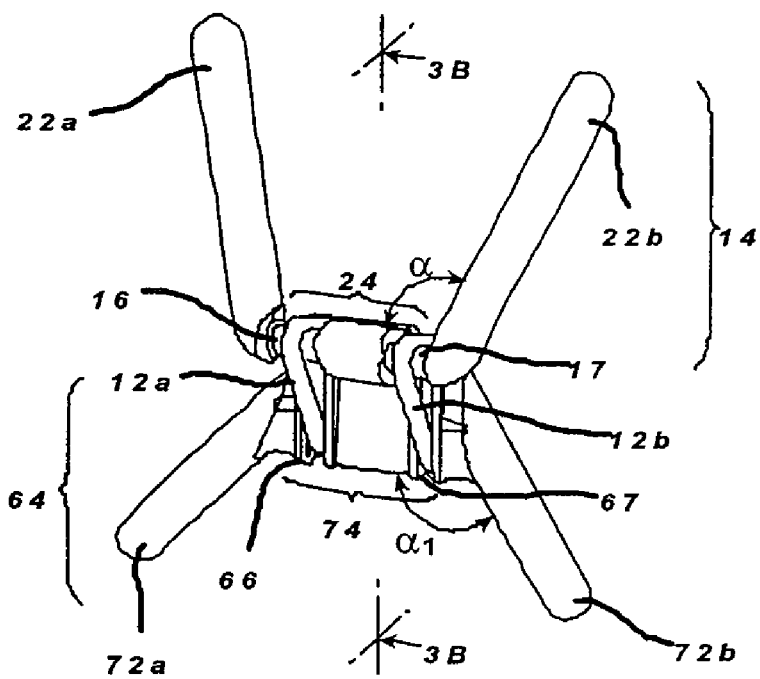
FIG. 3A is a perspective view of exemplary connection members and two artificial ligaments for use with the system of FIG. 2A.

The first connection member 14 can have any configuration that allows it to couple to a vertebra 30 while enabling the artificial ligament 12a, 12b to maintain slidable contact therewith. As shown in FIGS. 2A-2C, the first connection member 14 is adapted to couple to opposed pedicles 32, 34 of the superior vertebra 30 and to extend between the pedicles 32, 34. In this configuration a laminectomy is performed and the spinous process is removed. However, the configuration of the first connection member 14 can change when the spinous process is retained such that the connection member 14 passes inferior to the spinous process. By way of non-limiting example, the first connection member 14 can be substantially linear. Referring now to FIG. 3A, the first connection member 14 can be in the form of a substantially v-shaped or u-shaped rod that includes a central linear portion 24 with two lateral arms 22a, 22b extending at an angle α relative to the central portion 24. The angle α can vary depending on the size of the patient, and in particular depending on the distance between the opposed pedicles 32, 34 and the angle necessary to allow the first connection member 14 to extend around the spinous process.

The second connection member 64 can also have a variety of shapes and sizes, but it an exemplary embodiment it has a shape that is complementary to the shape of the first connection member 14, such that when coupled to the vertebrae 30, 80, together they form substantially an "x" configuration. This allows the first and second members 14, 64 to remain independent from one another, however at the same time articulate with respect to one another. Therefore, in this configuration, the first and second members 14, 64 contact and slide relative to one another, functioning as a facet joint replacement or augmentation device. Further, the artificial ligament 12a, 12b holds the first and second members 14, 64 together, thereby preventing separation thereof.

Thus, the second connection member 64 can also be in the form of a substantially v-shaped or u-shaped rod that includes a central portion 74 with two lateral arms 72a, 72b extending at an angle $α_1$ relative to the central portion 74. However, such a configuration is not necessary to avoid contact with the spinous process 86 of an inferior vertebra 80, as the central portion 74 can be positioned superior to the spinous process 87 of the inferior vertebra to allow the lateral arms 72a, 72b to mate to the pedicles 82, 84 of the inferior vertebra 80.

A variety of techniques can be used to attach the first and second connection members 14, 64 to the vertebrae 30, 80. In one exemplary embodiment, a mechanism 26a, 26b, 86a, 86b that allows for intra-operative adjustment of bone screw angulation, such as pedicle screws, can be used. Alternatively, the first and second connection members can each include one or more thru-bores formed near the distal end of the lateral arms for receiving one or more fastening elements, such as bone screws. One skilled in the art will appreciate that the thru-bores can have any configuration that allows them to receive a fastening element, and the configuration can vary depending on the type of fastening element used. The thru-bores can also incorporate a polyaxial mechanism of the type commonly used in pedicle screw systems that allows for intra-operative adjustment of bone screw angulation. Other fastening elements include, by way of non-limiting example, staples, rivets, hooks, wires, etc.

The connection members can also be configured such that an artificial ligament is adapted to be seated within the ligament seating region and slidably contact the connection members via a ligament contact region. Generally, the number of ligament seating regions a connection member can have is based upon the number of ligaments used in the system. For example, FIGS. 2A-3B illustrate an embodiment where two artificial ligaments 12a, 12b are used, and thus each connection member can have two ligament seating regions. While the ligament seating regions 16, 17, 66, 67 can be located at a variety of places on the first and second connection members 14, 64, as shown, the ligament seating regions 16, 17, 66, 67 are formed on opposed ends of the central portion 24, 74. Alternatively, FIG. 4 illustrates a system 110 where one artificial ligament 112 is used, and it therefore has one ligament seating region 116, 166 is formed on each of the first and second connection members 114, 164. While the ligament seating region 116, 166 can be located at a variety of locations, as shown it is substantially centrally located on the central portions 124, 174 of the first and second connection members 114, 164. This connection geometry, e.g., the substantially centrally located ligament seating region 116, 166, allows the system 110 to have a similar non-linear force-displacement relationship as discussed below with respect to the system of FIGS. 2A-3B.

While the ligament seating region can have any configuration that allows it to securely hold the artificial ligament, such that the artificial ligament will not dislocate, the exemplary ligament seating regions 16, 17, 66, 67, 116, 166 discussed above are grooves that are complementary in shape and depth to the artificial ligament 12a, 12b, 112. Alternatively, as will be discussed in more detail below with respect to FIGS. 8-13C, the ligament seating region can be part of a post system.

Generally, in order to effect the non-linear force-displacement, the ligament should contact the ligament seating region in one more region than bone segments connected. Thus, as shown in FIGS. 2A-3B, since two bone segments 30, 80 are being connected, the ligament 12a, 12b should contact each corresponding ligament seating region 16,66 and 17,67 of the connection members 14, 64 at least at three ligament contact regions in order to effect the non-linear force displacement relationship of the artificial ligament.

Figure 3B:
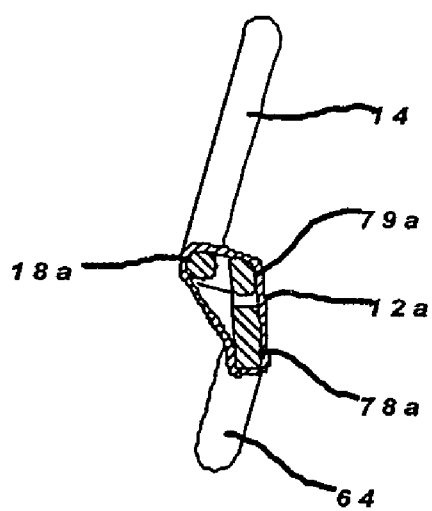
FIG. 3B is a cross-sectional view of the connection members of FIG. 3A taken across line B-B.
Figure 4:
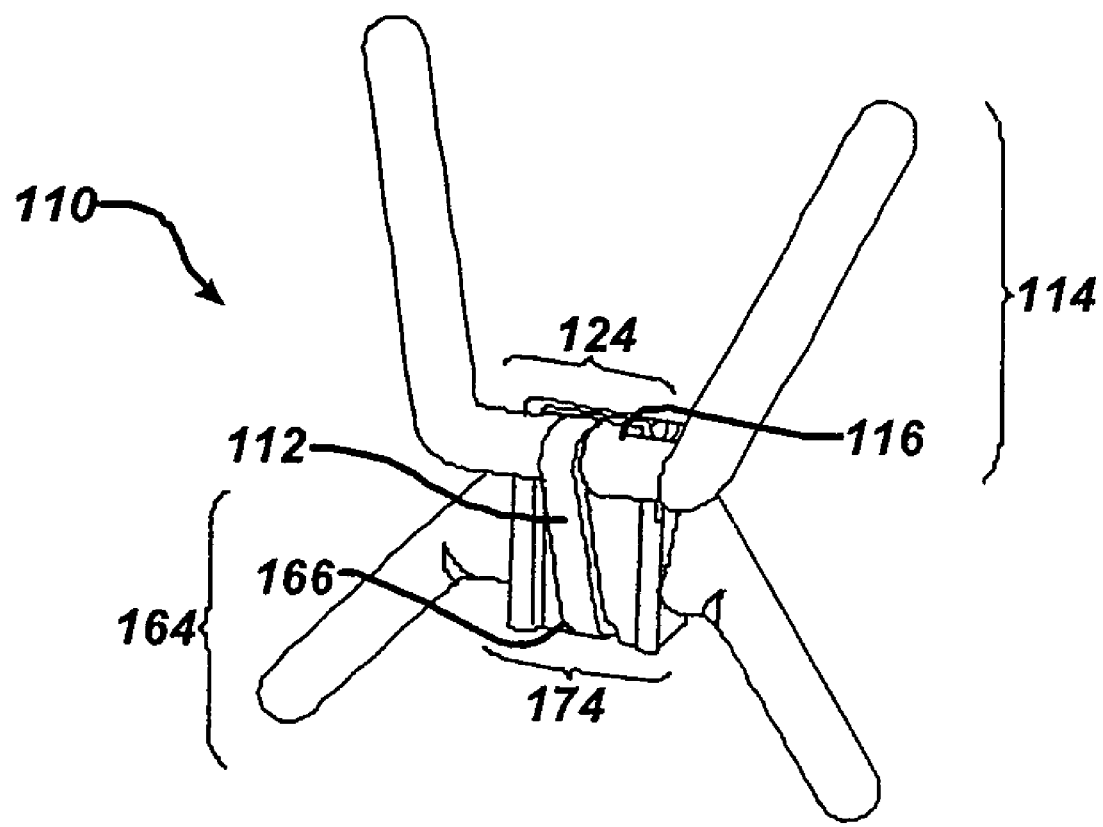
FIG. 4 is a perspective view of connection members and an artificial ligament according to another embodiment.

While the at least three ligament contact regions can be equivalent in size, for systems that use two connection members, such as the system shown in FIG. 3B, the ligament contact region on the first connection member 14 can have a surface area that is less than the surface area of the ligament contact region of the second connection member 64. This allows the two connection member system to have at least three ligament contact regions, at least one ligament contact region 18a located on the first connection member 14 and at least two ligament contact regions 78a, 79a located on the second connection member 64.

The ligament contact regions can have any configuration that allows the friction between the artificial ligament and the surface of the connection member to be minimized to an amount that is preferably as close to zero as possible when the ligaments slide thereover. In one embodiment, the ligament contact region can be a portion of the smooth surface of the ligament seating region. Alternatively, if the ligament seating region has a shape that is rectangular, or some other non-curved shape, a portion of the ligament seating region can include a curved surface to allow for ligament contact with ease of sliding and reduced friction. Moreover, the ligament contact region can include a pulley or a pivot system, as will be discussed in more detail below.

The artificial ligament can form the closed loop in a variety of ways. In one embodiment, and still referring to FIGS. 3A-3B, the artificial ligament 12a, 12b is looped around the ligament seating regions 16, 17, 66, 67 of the first and second connection members 14, 64, and does not attach directly to either the first or second connection member 14, 64, but rather is sutured, stapled, or knotted to itself. However, it is not necessary that the artificial ligament be in the form of a closed loop that connects to itself. In another embodiment both ends of the artificial ligament can fixedly attach to the first connection member by any suitable fastening device or technique known in the art, such as a fastener. This connection prevents or limits movement (e.g., sliding) of the artificial ligament relative to the first connection member. The artificial ligament is not fixedly attached to the second connection member, but rather loops around it such that the artificial ligament is able to slide relative thereto. For example, the second connection member acts like a pulley and redirects the motion of the artificial ligament. Alternatively, this attachment configuration can be reversed such that the artificial ligament is fixedly attached to second connection member and is looped around the first connection member.

Figure 5A:
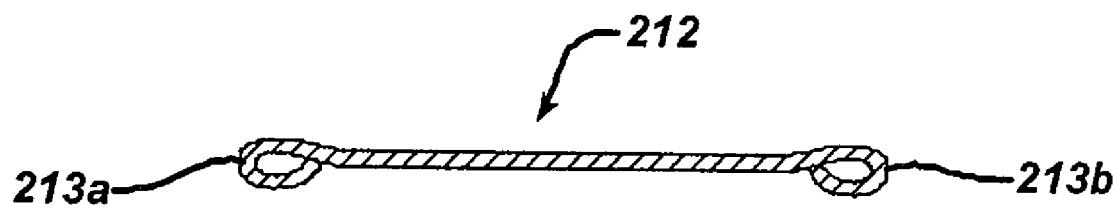
FIG. 5A is a plan view of an exemplary artificial ligament.
Figure 5B:
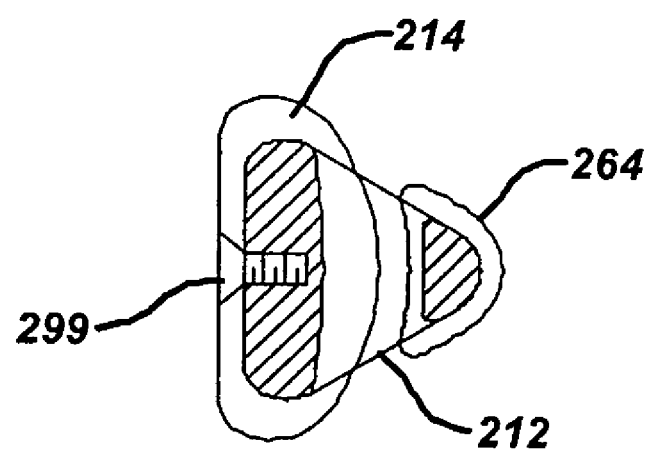
FIG. 5B is a schematic showing the ligament of FIG. 5A coupled between connection members according to one embodiment.

The artificial ligament can also optionally have features that assist in fastening it to the connection members. As shown in FIG. 5A, the artificial ligament 212 can have eyelets 213a, 213b that are adapted to receive a fastener, e.g., a screw, to assist in attaching the artificial ligament to the connection member. As a result, the closed loop can be formed by looping the artificial ligament 212 around the second connection member 264, and then securing it to the first connection member 214 by a fastener 299, as shown in FIG. 5B. This is particularly advantageous in that it allows the surgeon to more precisely govern the range of motion of the artificial ligament by tightening or loosening the fastener.

Figure 6A:
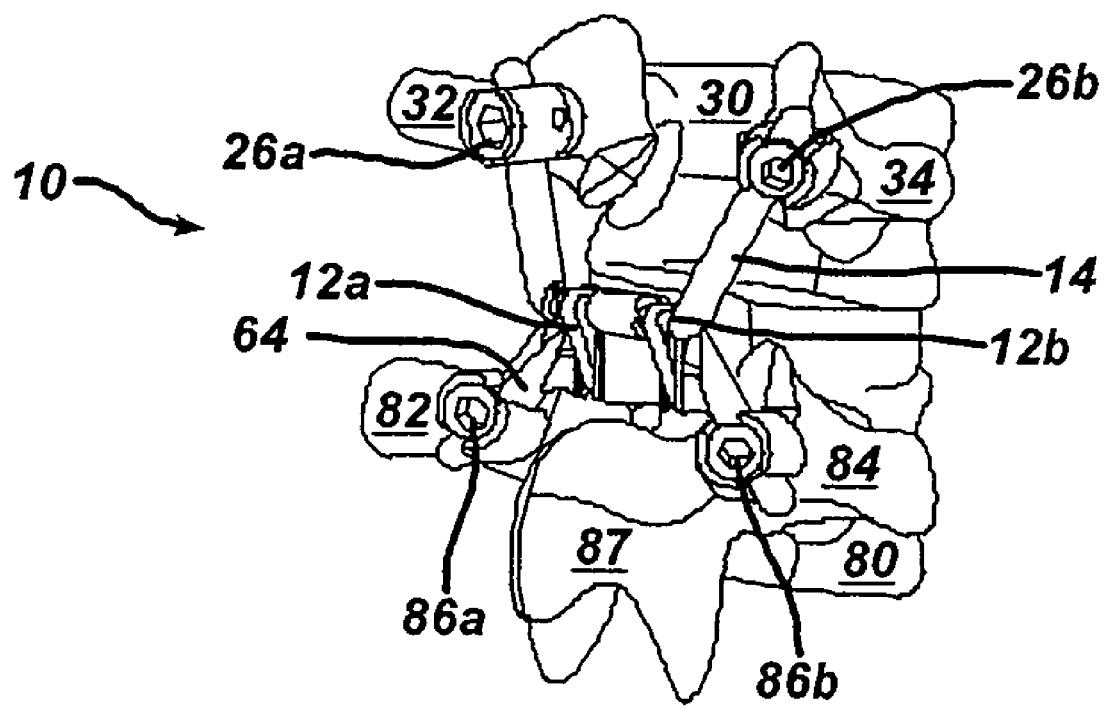
FIG. 6A is a perspective view of the system of FIG. 2A in flexion.
Figure 6B:
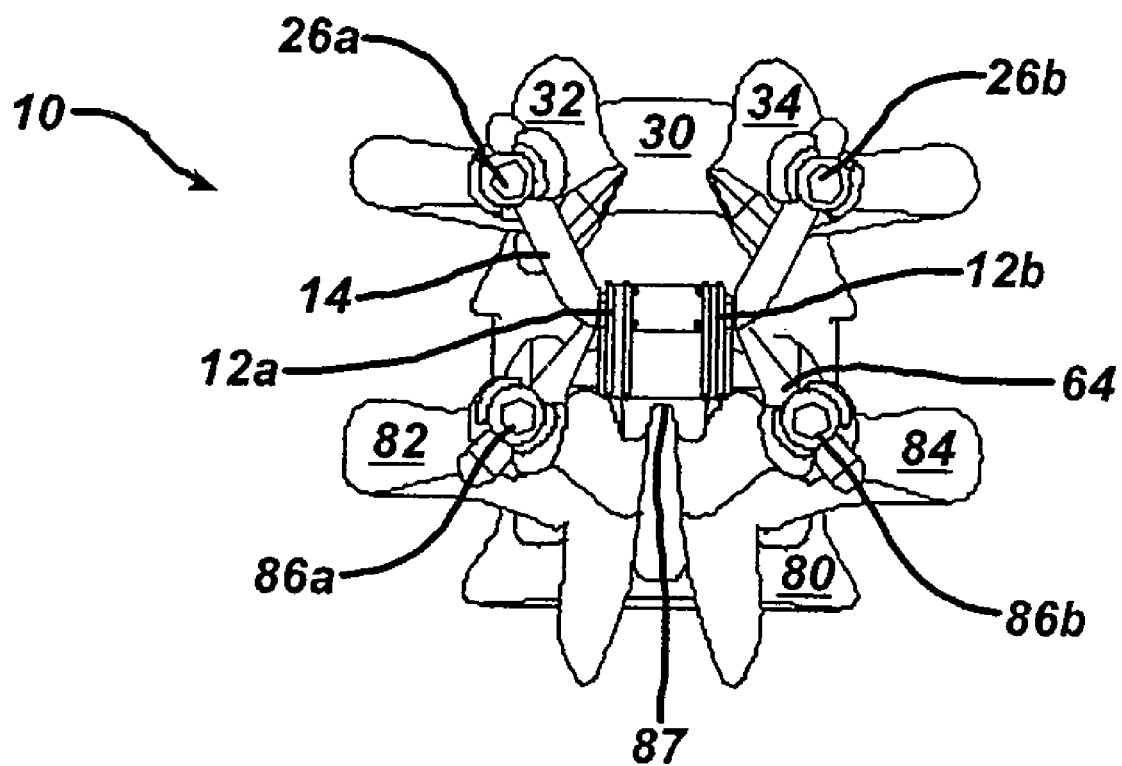
FIG. 6B is a posterior view of the system of FIG. 6A.
Figure 6C:
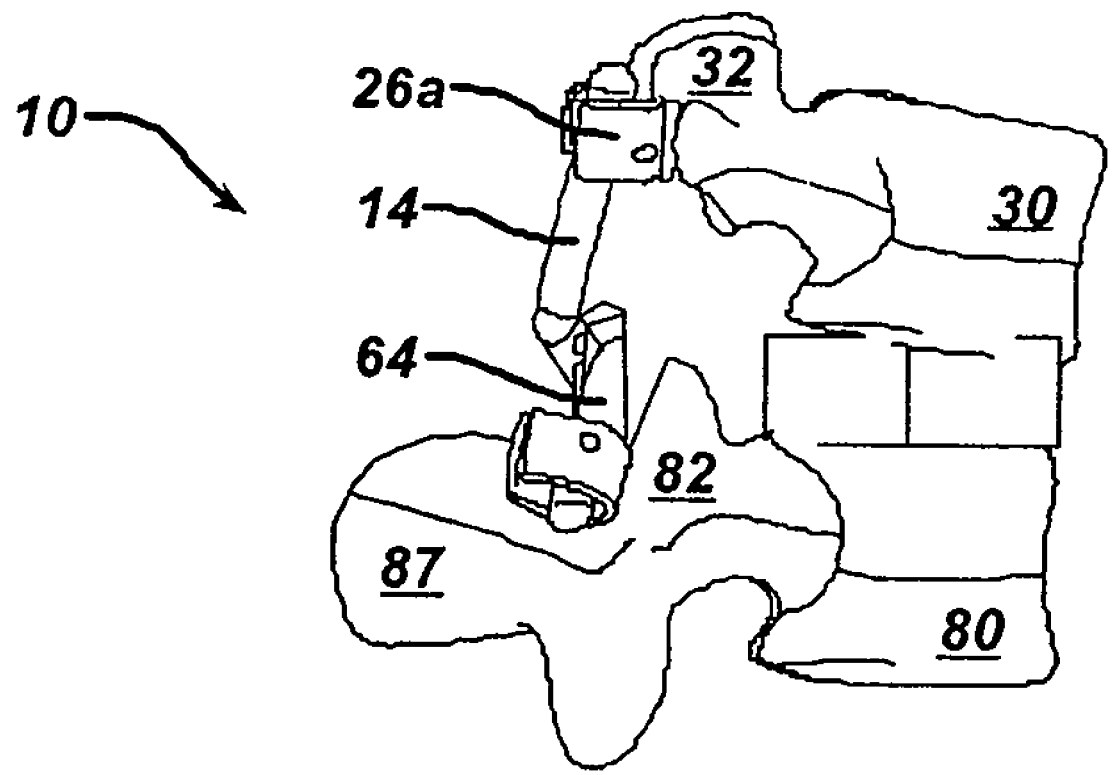
FIG. 6C is a side view of the system of FIG. 6A.
Figure 7A:
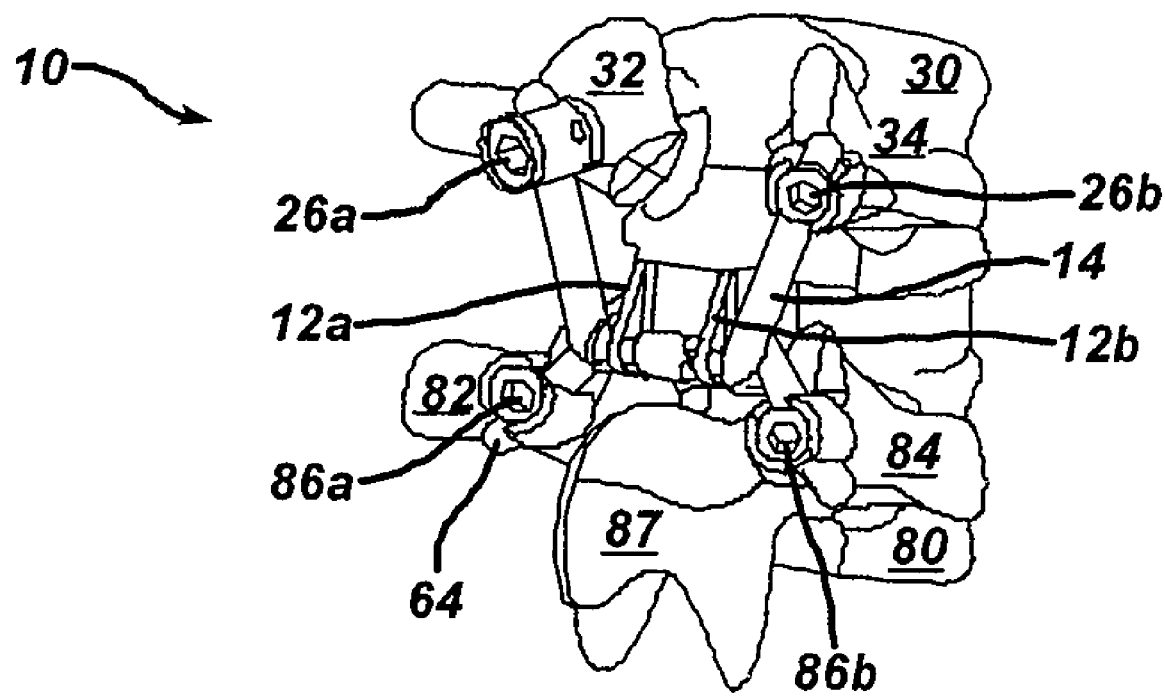
FIG. 7A is a perspective view of the system of FIG. 2A in extension.
Figure 7B:
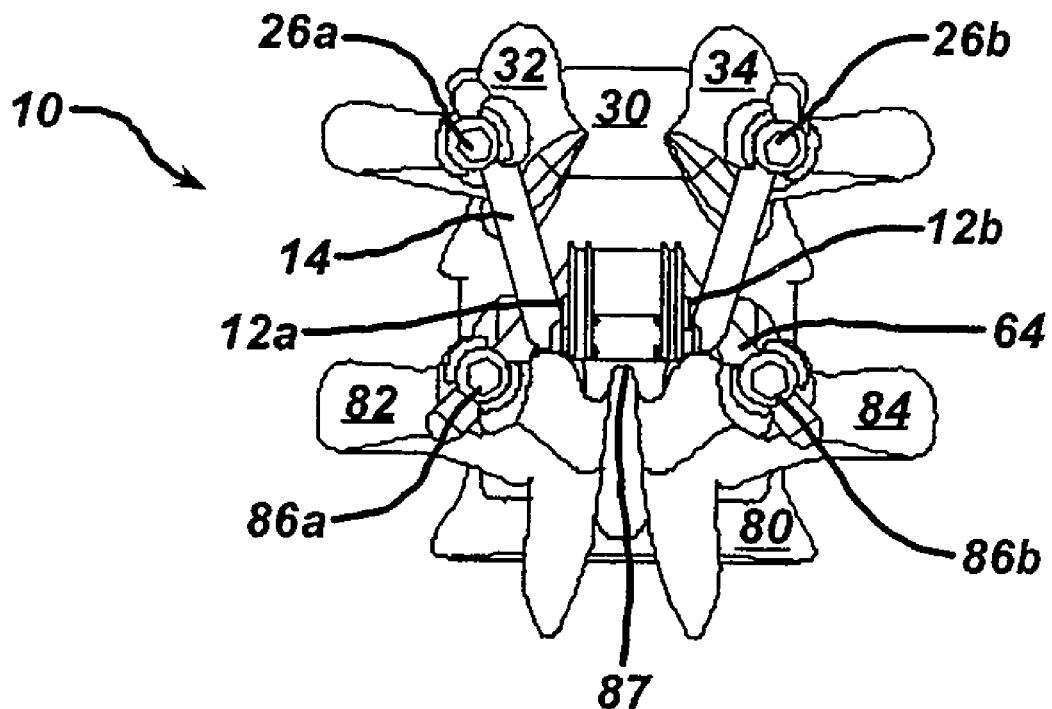
FIG. 7B is a posterior view of the system of FIG. 7A.
Figure 7C:
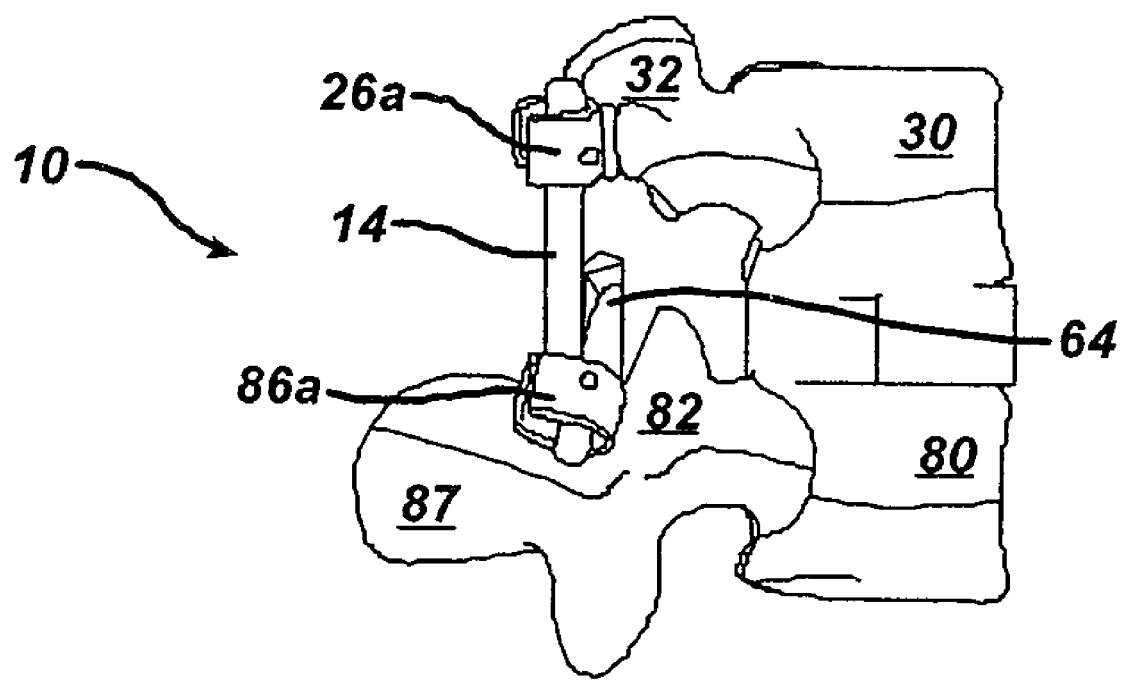
FIG. 7C is a side view of the system of FIG. 7A.

As a result of the artificial ligament-connection member combination, the artificial ligament system can exhibit a non-linear force-displacement relationship, similar to that of a natural ligament shown in FIG. 1. For example, and referring back to FIGS. 2A-2C, the system 10 is in a neutral position has low stiffness, and stiffness continues to be low with the initial motion (e.g., in flexion and extension). However, as the amount of motion increases, the stiffness of the system 10 increases. Thus, as shown in FIGS. 6A-6C, as movement of the vertebrae 30, 80 forces the first connection member 14 upwards, to a position of about 10 degrees of flexion, the second connection member 64 moves relative to the first connection member 14 and the artificial ligament 12a, 12b slides over the second connection member 64. As it does so, and as a result of the flexion, the length of the artificial ligament 12a, 12b increases by about 2%. Moreover, the stiffness of the system 10 increases requiring more force to produce additional movement. In a like manner, as movement of the vertebrae 30, 80 forces the first connection member 14 in the downward direction to a position of about 5 degrees extension, shown in FIGS. 7A-7C, the length of the artificial ligament 12a, 12b is also increased by about 2% and the stiffness of the system 10 increases. Therefore, a small stretch of about 2% in the artificial ligament allows large motion of about 10 degrees in flexion and about 5 degrees in extension.

While FIGS. 2A-2C and 6A-7C illustrate a system 10 where a patient is allowed about 10 degrees in flexion and about 5 degrees in extension, one skilled in the art will appreciate that a surgeon can adjust the tension of the artificial ligament to produce a desired degree of ligament stretch. For example, if the surgeon desires that there be less motion, or a limited range of motion, the patient can be allowed, for example, about 6 degrees of flexion and about 3 degrees of extension. Alternatively, if the surgeon desires that the patient have a range of motion that is closer to the normal range of motion, the surgeon can adjust the tension of the artificial ligament such that the patient has about 16 degrees of flexion and 8 about degrees of extension.

As discussed above with respect to FIGS. 2A-3B, the location and the number of ligament contact regions influence the overall range and stiffness of the artificial ligament system 10. In the following FIGS. 8A-13C, the ligament contact region is simply represented by posts where the ligament wraps around. Although the post system can be an example of a physical model, the posts serve as simple representation of the ligament contact regions in FIGS. 8A-13C. Furthermore, the contact between the two bones in FIGS. 8A-13C can be a natural joint (e.g., hip, knee, shoulder, etc.) or an artificial joint prosthesis.

When the post systems are used as an actual embodiment, the post systems can be formed as part of first and second connection members that are similar to the first and second connection members 14, 64 discussed above with respect to FIGS. 2A-3B. The post systems can optionally be attached directly to the bone, e.g., the superior and inferior vertebrae. Such post systems can be attached to the bone by any way known in the art, such as by fasteners, staples, etc. In an exemplary embodiment the post systems are attached to the bone by fasteners, such as bone screws.

Figure 8A:
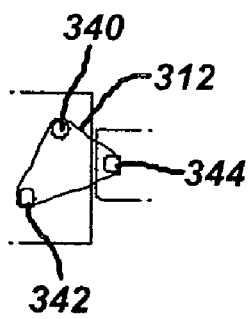
FIGS. 8A-12 are schematics shown other exemplary systems for stabilizing bone segments as disclosed herein.
Figure 8B:
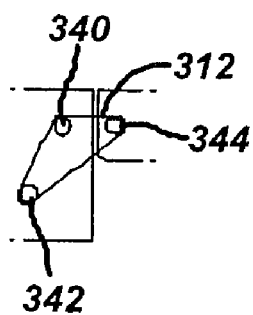
Figure 8C:
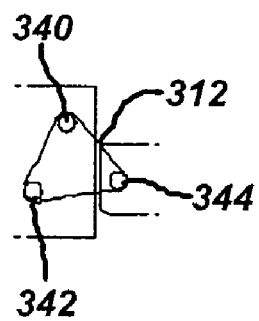

In addition to providing a non-linear force-displacement, the posts and artificial ligaments can be configured to achieve a variety of ligament stretches and strengths based on the number of posts as well as the configuration thereof. Posts 340, 342, 344 can be arranged in a variety of triangular configurations depending upon the desired force-displacement relationship, as well as the desired stretch and strength of the artificial ligament 312. For example, FIG. 8A represents the neutral position of two bones and posts 340, 342, 344. As the bone with post 344 moves upward as in FIG. 8B, the artificial ligament 312 stretches less compared to the downward movement as in FIG. 8C. Therefore, the upward movement produces less stiffness than the downward movement, and different stiffnesses for different movement directions can be produced by locating the posts (and contact regions) at various positions.

Figure 9:
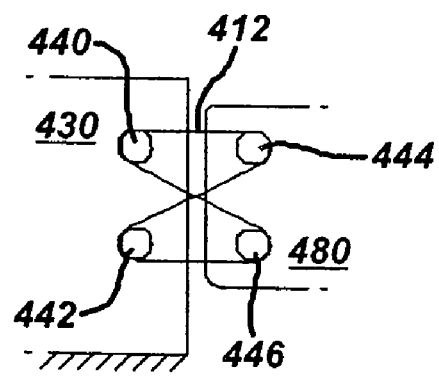

Conversely, the greater the number of posts that a given system has, such as the four post system of FIG. 9, the longer the artificial ligament that is required. This results in an artificial ligament that has a lower stiffness and greater movement. As shown, the posts 440, 442, 444, 446 are placed complementary to one another on the respective bone segments 430, 480 such that when the artificial ligament 412 is looped between the first and third 440, 444 and the second and fourth posts 442, 446, a substantially x-shaped configuration results.

While the posts can have any shape, such as substantially cylindrical, substantially rectangular, etc., in an exemplary embodiment the posts are substantially cylindrical. Similar to the first and second connection members discussed above with respect to FIGS. 2A-7C, the posts can have a ligament seating region that helps ensure that the artificial ligament remains seated on the post. While this ligament seating region can have a variety of configurations, in an exemplary embodiment it can be a groove similar to the grooves discussed above. Alternatively, the ligament seating region of the post can also include any other configuration that prevents the artificial ligament from dislocating from the post, such as a stop formed along the outer perimeter, e.g., the end of the post farthest from the bone, or a bore formed therein.

Figure 10:
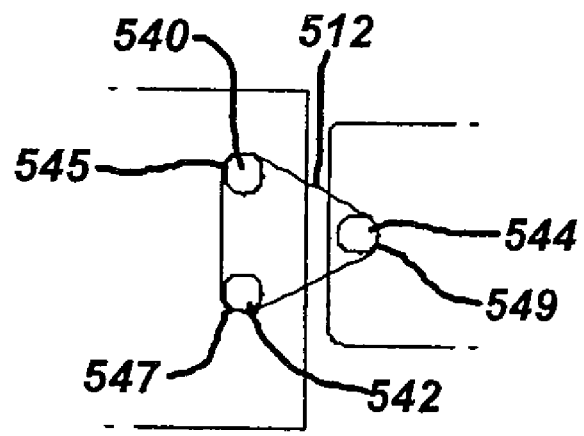
Figure 11:
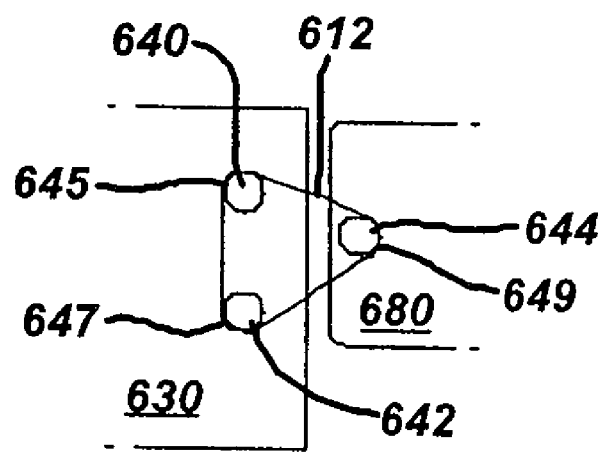

The ligament contact region can be a portion of the smooth surface of the post, or alternatively as shown in FIG. 10, a curved surface 545, 547, 549 formed on a portion of a post 540, 542, 544. While the curved surfaces 545, 547, 549 can be located in a variety of places on the posts 540, 542, 544, in an exemplary embodiment shown in FIG. 10, the curved surfaces 545, 547, 549 are located along the outer perimeter thereof. The ligament contact region can also include a rotatable member, such as a pulley system, shown in FIG. 11. While the pulley system can include any combination of pulleys and/or posts, an exemplary pulley system includes one post 644 having a pulley 641 formed thereon and two posts 640, 642 having curved surfaces 645, 647 that are attached to the first and second bone segments 630, 680. One skilled in the art will appreciate that the pulley 641 can be attached to a post 644 as shown, or it can be attached directly to the bone segment.

Figure 12:
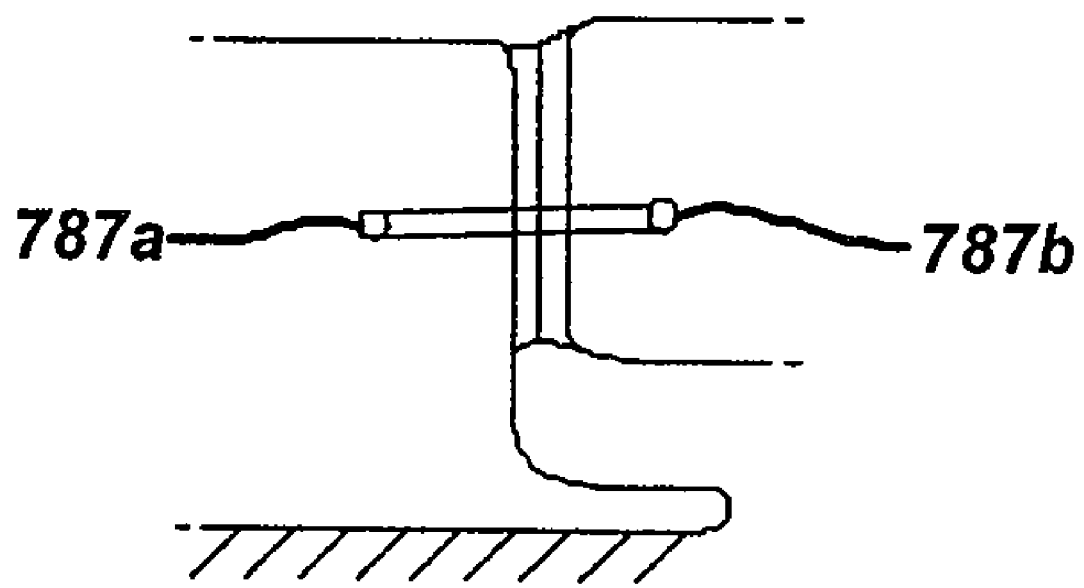

While the pulley 641 can have any configuration, generally it has a configuration that is similar to pulleys known in the art, that is, a cylindrical surface with at least one bearing inside to receive the artificial ligament 612. Moreover, the pulley system can be a cam system with varying distance from the ligament to the center of rotation. Alternatively, the ligament contact region can be part of a pivot point, such as a hinge joint, 787a, 787b, as shown in FIG. 12.

Figure 13A:
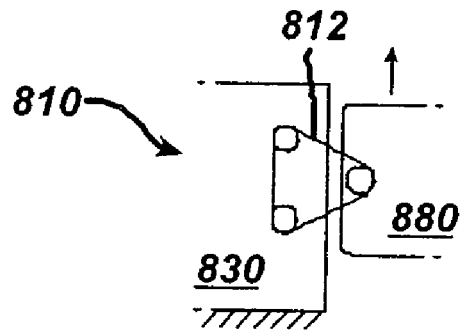
FIGS. 13A-13C are schematic views of additional exemplary systems for stabilizing bone segments in a neutral position (FIG. 13A); in flexion (FIG. 13B); and in extension (FIG. 13C).
Figure 13B:
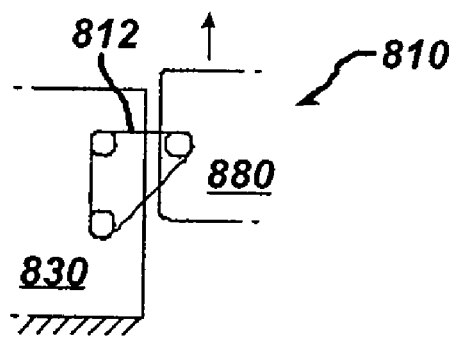
Figure 13C:
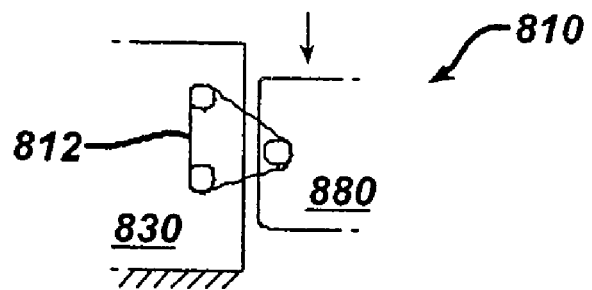

Similar to embodiments discussed above with respect to FIGS. 2A-2C and 6A-7C, the ligaments coupled to the post system also exhibit a non-linear relationship between motion and force where the stiffness is low with the initial motion and increases with greater motion. For example, as shown in FIG. 13A, when the system 810 is in a neutral position, the artificial ligament 812 has a low stiffness. However, as the motion increases to either the flexion or extension positions as a result of movement by either the first or second bone segment 830, 880, as shown in FIGS. 13B-13C, respectively, the stiffness of the system increases, such that large motion is possible with a low stretch artificial ligament 812.

One skilled in the art will appreciate that the first and second connection members, posts, pulleys, and/or hinge joints can be formed from a variety of materials, but preferably they are substantially rigid. In an exemplary embodiment, they are formed from a bioimplantable metal, such as titanium, stainless steel, and cobalt and nickel based alloys, such as cobalt-chromium-molybdenum (Co—Cr Mo).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for stabilizing adjacent bone segments, comprising:
   at least one artificial ligament configured to couple at least two connection members;
   a first connection member having first and second arms configured to be coupled to a first bone segment and having a first central element extending between the first and second arms with at least one first ligament seating region formed around the first central element for receiving the at least one ligament, the at least one first ligament seating region having at least one ligament contact region with a first surface area; and
   a second connection member having first and second arms configured to be coupled to a second bone segment and having a second central element positioned in contact with the first central element and extending between the first and second arms with at least one second ligament seating region formed around the second central element, the at least one second ligament seating region having at least two ligament contact regions with a second surface area,
   wherein the at least one ligament is slidably disposed within the first and second ligament seating regions to contact the ligament contact regions of the first and second connection members such that the artificial ligament exhibits a non-linear force displacement relationship.

2. The system of claim 1, wherein the first surface area is less than the second surface area such that the at least two ligament contact regions are located at opposed edges of the ligament seating region of the second connection member.

3. The system of claim 1, wherein the ligament is configured in the form of a closed loop.

4. The system of claim 1, wherein the bone segments are adjacent vertebrae.

5. The system of claim 1, wherein the at least one artificial ligament is a polymer fiber.

6. The system of claim 5, wherein the polymer is polyethylene, polyester, polypropylene, polyaramide, or any combination of thereof.

7. The system of claim 1, wherein the at least one artificial ligament has a stretch that is less than 5%.

8. The system of claim 1, wherein the at least one artificial ligament has a tensile strength that is greater than about 100N.

9. The system of claim 1, wherein the at least one artificial ligament has opposed first and second ends, and an eyelet formed on each end, such that the closed loop can be formed by inserting a fastener through the eyelets.

10. The system of claim 1, wherein the first and second connection members are adapted to articulate relative to one another.

11. The system of claim 1, wherein the first and second connection members are in the form of substantially V-shaped connectors adapted to be positioned on a posterior surface of a first and second vertebrae.

12. The system of claim 1, wherein the ligament seating region is a groove that is adapted to slidably receive the at least one artificial ligament.

13. The system of claim 1, wherein the ligament seating region is a post that is adapted to slidably receive the at least one artificial ligament.

14. The system of claim 13, wherein the post has a groove formed therein for receiving the at least one artificial ligament.

15. The system of claim 13, wherein the post has a stop formed at an end thereof for receiving the at least one artificial ligament.

16. The system of claim 1, wherein the ligament contact region is a pulley.

17. The system of claim 1, wherein the ligament contact region is a pivot point.

18. The system of claim 1, further comprising at least three ligament contact regions.

* * * * *